United States Patent [19]

Bouillon et al.

[11] Patent Number: 4,671,956
[45] Date of Patent: Jun. 9, 1987

[54] ANTIACNE COMPOSITION CONTAINING BENZOIC PEROXIDE IN ASSOCIATION WITH AT LEAST ONE SUN FILTER

[75] Inventors: Claude Bouillon, Eaubonne; Gerard Lang, Epinay Sur Seine; Jean-Pierre Laugier, Antony, all of France

[73] Assignee: L'Oreal, Paris, France

[21] Appl. No.: 919,611

[22] Filed: Oct. 14, 1986

Related U.S. Application Data

[63] Continuation of Ser. No. 677,382, Dec. 3, 1984, abandoned.

[30] Foreign Application Priority Data

Dec. 1, 1983 [LU] Luxembourg ............................ 85111

[51] Int. Cl.$^4$ .......................... A61K 7/42; A61K 7/44
[52] U.S. Cl. ........................................ 424/59; 424/47; 424/60; 514/859; 514/941
[58] Field of Search ................... 514/859; 424/59

[56] References Cited

U.S. PATENT DOCUMENTS

| | | | |
|---|---|---|---|
| 4,056,611 | 11/1977 | Young | 514/714 |
| 4,261,982 | 4/1981 | Luedders et al. | 514/859 |
| 4,299,826 | 11/1981 | Luedders | 514/859 |
| 4,318,907 | 3/1982 | Kligman et al. | 514/859 |
| 4,361,584 | 11/1982 | Fulton, Jr. | 514/714 |
| 4,411,893 | 10/1983 | Johnson et al. | 514/714 |
| 4,421,739 | 12/1983 | Bouillon et al. | 424/59 |
| 4,443,442 | 4/1984 | Skillern | 514/859 |
| 4,497,794 | 2/1985 | Klein et al. | 514/859 |
| 4,507,287 | 3/1985 | Dixon | 514/859 |
| 4,514,385 | 4/1985 | Damani et al. | 514/859 |

FOREIGN PATENT DOCUMENTS 465188 6/1937 United Kingdom ................. 424/62

OTHER PUBLICATIONS

Sagarin, Cosmetics Science and Technology, 1957, pp. 200 and 201.

Primary Examiner—Dale R. Ore
Attorney, Agent, or Firm—Wegner & Bretschneider

[57] ABSTRACT

There is disclosed a composition for the local treatment of acne containing from 0.5 to 20% by weight of benzoyl peroxide in association with at least one sun filter that is benzylidenecamphor and its derivatives, 2-phenylbenzimidazole-5-sulfonic acid and its salts, 2-hydroxybenzenophenone and its derivatives, $C_2$–$C_{12}$ alkyl p-dimethylaminobenzoates, salicylic acid esters, dibenzoylmethane derivatives and cinnamic acid derivatives.

5 Claims, No Drawings

ANTIACNE COMPOSITION CONTAINING BENZOIC PEROXIDE IN ASSOCIATION WITH AT LEAST ONE SUN FILTER

This application is a continuation of U.S. application Ser. No. 677,382, filed Dec. 3, 1984, now abandoned.

BACKGROUND OF THE INVENTION

The present invention is directed to a new antiacne composition containing benzoyl peroxide in association with at least one sun filter; the latter, while permitting a better stabilization of the benzoyl peroxide, leads to a better tolerance by the different types of skin as a function of the environmental conditions to which they may be subjected.

DISCUSSION OF THE PRIOR ART

Among the various therapeutic agents recommended in the treatment of acne, benzoyl peroxide has already proven for many years to be a particularly powerful keratolytic agent, also endowed with antibacterial properties.

However, the use of benzoyl peroxide presents some drawbacks as a result of its instability, its reactivity, and its side effects.

Included among its side effects, benzoyl peroxide exhibits a certain aggressiveness capable of causing frequent intolerances in the course of treatment, such as itching, even when benzoyl peroxide is used at relatively low concentrations.

In order to avoid the side effects of benzoyl peroxide, it has already been proposed to associate it with certain agents such as, for example, salicyclic acid or derivatives of guanidine, but those compositions have not succeeded in leading in a completely satisfactory way to an appreciable amelioration of the aggressiveness and of the skin sensitization phenomena deriving therefrom.

In fact, the observed side effects do not seem to be due uniquely to the benzoyl peroxide itself, but rather to certain decomposition products of the other compounds present in the compositions; the decomposition of the latter compounds is caused essentially by the strong reactivity of the benzoyl peroxide.

GENERAL DESCRIPTION OF THE INVENTION

Applicants, after much research, have ascertained in an entirely surprising way that it is possible to obtain antiacne compositions that are particularly stable in time and that are endowed with better tolerance by the different types of skin, even with respect to skins that are particularly sensitive to benzoyl peroxide, by associating that keratolytic agent with certain well-determined classes of sun filters or screens.

It has been ascertained that the compositions containing such sun filters exhibit good stability in time and permit the treating of the different types of acne, notably on the face, without encountering the intolerance phenomena of the known compositions currently used in the treatment of acne.

It has also been ascertained that the antiacne compositions with a base of benzoyl peroxide and at least one sun filter exhibit a more reliable and more durable activity and that their use is safer than previous compositions containing benzoyl peroxide. Moreover, by preventing deterioration of the benzoyl peroxide, the compositions are better tolerated by the different types of skin. The skins thus treated with the compositions according to the present invention are less fragile and sensitive to external aggressive factors, such as light rays, than they would be if they were treated with benzoyl peroxide alone.

DETAILED DESCRIPTION OF THE INVENTION

The present invention is directed to a new composition for the local treatment of acne, containing from 0.5 to 20% by weight of benzoyl peroxide and at least one sun filter taken from the group consisting of benzylidenecamphor and its derivatives, 2-phenyl-benzimidazole-5-sulfonic acid and its salts, 2-hydroxybenzophenone and its derivatives, alkyl p-dimethylaminobenzoates, the alkyl radical having from 1 to 12 carbon atoms, the esters of salicyclic acid, the derivatives of dibenzoylmethane, and the derivatives of cinnamic acid.

These different sun filters, among the numerous known and utilized sun filters, are the only ones that have proved to exhibit a stabilizing action with respect to benzoyl peroxide, thus preventing the irritation phenomena entailed by the use of that keratolytic agent.

According to the invention, the benzoyl peroxide concentration is preferably between 2.5 and 10% and that of the sun filter between 0.1 and 10% by weight with respect to the total weight of the composition. The benzoyl peroxide is used in the form of finely divided powder, in the dry or moist state, preferably in the moist state.

The benzylidenecamphor and its derivatives are represented by the following general formula:

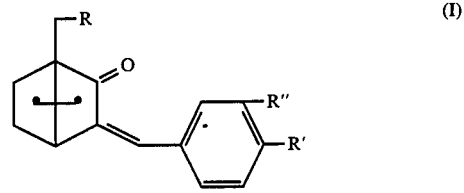

wherein:

R represents a hydrogen atom, the —SO$_3$H radical and its salts or a —SO$_2$NH—R$_1$ radical, R$_1$ representing a linear or branched alkyl radical having from 1 to 12 carbon atoms, preferably a 2-ethylhexyl radical or a protein residue such as a derivative of keratin, collagen, gelatin, albumin, casein, or lactalbumin, R' represents a hydrogen atom; an alkyl radical having from 1 to 4 carbon atoms; a substituted or nonsubstituted alkoxy radical having from 1 to 8 carbon atoms; a quaternary ammonium, preferably the —⊕N(CH$_3$)$_3$ radical; the —SO$_3$H radical and its salts; a —SO$_2$NH—R$_2$ radical, R$_2$ representing a 2-ethylhexyl radical or a keratinyl radical; a —CH=C(CO$_2$R$_3$)$_2$ radical, R$_3$ representing an alkyl radical having from 1 to 12 carbon atoms; a radical:

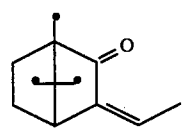

or a radical:

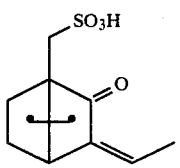

and

R″ represents a hydrogen atom, an alkoxy radical having from 1 to 4 carbon atoms, or the —SO₃H radical and its salts when R' represents an alkyl or alkoxy radical.

These sun filters are described more particularly in the following U.S. Pat. Nos.: 3,781,417; 4,061,730; 4,165,336; 4,250,108; 4,290,974; 4,304,730; 4,323,549; 4,327,031; 4,330,488; 4,406,880; and 4,421,739; and in the following United Kingdom Pat. Nos.: 2,121,801; 2,123,418; and 2,128,195. The disclosures of each of the above patents are incorporated herein by reference.

Among the derivatives of benzylidenecamphor covered by the general formula (I) above, those that have led to particularly advantageous results are the following:

p-tolylidenecamphor, trimethylammoniobenzylidenecamphor methyl sulfate, 4-isopropylbenzlidenecamphor, 4-[2-oxo-3-bornylidene-methyl]benzenesulfonic acid and its salts, 2-methyl-5-(2-oxo-3-bornylidene-methyl)benzenesulfonic acid and its salts, N-(2-ethylhexyl)-3-benzylidene-10-camphosulfonamide, 3-[4-(2-oxo-3-bornylidene-methyl)benzylidene]-10-camphosulfonic acid and its salts, 1,4-bis-phenylene(3-methylene-10-camphosulfonic)acid and its salts, ethyl p-(2-oxo-3-bornylidene-methyl)benzylidenemalonate, p-methoxy-3-benzylidene-10-camphosulfonic acid and its salts, 3-[4-(2-hydroxy-3-morpholinopropoxy)benzylidene]-2-oxo-10-bornanesulfonic acid and its salts, N-keratinyl-2-oxo-3-bornylidene-benzenesulfonamide, N-(2-ethylhexyl)-p-methoxy-3-benzylidene-10-camphosulfonamide and 4'-butoxy-3'-methoxy-3-benzylidene-2-oxobornane.

Among the derivatives of 2-hydroxybenzophenone, one can mention, in particular, 2-hydroxy-4-methoxybenzophenone, 2-hydroxy-4-methoxybenzophenone-5-sulfonic acid and its salts, 2,2'-dihydroxy-4-methoxybenzophenone and the sodium salt of 2,2'-dihydroxy-4,4'-dimethoxybenzophenone-5-sulfonic acid.

Among the alkyl p-dimethylaminobenzoates, one can mention, in particular, 2-ethylhexyl p-dimethylaminobenzoate.

Among the esters of salicylic acid, one can mention homomenthyl salicylate and 2-ethylhexyl salicylate.

Among the derivatives of dibenzoylmethane, one can cite 4-isopropyldibenzoylmethane.

Among the derivatives of cinnamic acid are the salts and the esters such as diethanolamine p-methoxycinnamate and 2-ethylhexyl p-methoxycinnamate.

The salts of the compounds enumerated hereinabove are preferably the salts of sodium, potassium, or alkanolamines.

In the compositions of the invention, the sun filters can be associated with metallic oxides so as to obtain a total screen. Among these oxides one can cite te oxides of zinc and of titanium and, in particular, the oxide of titanium known under the name of "Rutile" and the oxides of titanium covered with mica, such as the product sold by the MEARL Corp. under the name of "TIMICA".

The antiacne compositions of the invention can be presented in different forms, notably in the form of an ointment, a gel, an emulsion, a lotion, or an aerosol.

The term "ointment" covers formulations such as creams having absorbable oleaginous bases, e.g., vaseline, lanolin, polyethyleneglycols, and their mixtures.

The emulsions, whether they are of the oil-in-water or water-in-oil type, are prepared by dispersing the benzoyl peroxide in the aqueous phase; the sun filter which is associated with it being dispersed, depending on its affinity, either in the fatty phase or in the aqueous phase before being put into emulsion form.

The ratio by weight of the fatty phase to the aqueous phase is generally between 95:5 and 25:75.

Among the different oils able to constitute the fatty phase, one can use various products such as:

animal oils such as, for example, lanolin, perhydrosqualene, vegetable fats such as sweet almond oil, avocado oil, castor oil, olive oil, grape-pip oil, poppyseed oil, colza oil, peanut oil, corn oil, sunflower seed oil, hazlenut oil, jojoba oil, safflower oil, wheatgerm oil, karite butter, and shorea robusta fat, and mineral oils such as, for example, paraffin oil, and silicone oils soluble in the other oils.

One can also use certain synthetic products such as, for example, saturated esters and notably isopropyl palmitate, isopropyl-, butyl- or cetylmyristates, hexadecyl-, glycerol- and polyethyleneglycol stearates, ethyl palmitate, as well as triglycerides, octanoic and decanoic acids, cetyl ricinoleate, purcellin oil and hydrogenated polyisobutene.

The fatty phase of the emulsions can also contain certain waxes, notably carnauba wax, beeswax, ozokerite, or candelilla wax.

These compositions, in emulsion form, can also contain other ingredients such as preservatives, pigments, perfumes, coloring agents, emulsion stabilizers such as magnesium sulfate, fillers such as talc, powders of nylon, of starch, of polyethylene, and the like.

The gels are semi-solid preparations obtained by gelatinization of a suspension of benzoyl peroxide and the sun filter with the aid of a gelatinizing agent such as "bentone gel" sold by N.L. INDUSTRIES, for a fatty phase, or, for an aqueous phase, reticulated polyacrylic acid such as that sold by the GOODRICH company under the name of Carbopol 940 or 941 and used in neutralized form, or else cellulose derivatives.

If one so desires, one can introduce into the gel a nonionic surfactant such as, for example, a polyoxyethylene alcohol comprising from 4 to 20 repeating units of ethylene oxide, or esters of sorbitan, which permits a better dispersion and availability of the benzoyl peroxide. One can also incorporate a solvent such as a lower aliphatic alcohol, like ethanol, in a proportion of 0.5 to 30% by weight, a preservative, a perfume, a coloring agent, and the like.

The composition according to the invention can also contain a humectant in a proportion of from 1 to 20%, such as, for example, glycerol, sorbitol, or propyleneglycol.

According to a preferred embodiment, the benzoyl peroxide can be associated with at least one antiacne substance usable topically, notably an antibiotic substance.

According to this feature of the invention, the antibiotic substance is generally present at a concentration of between 0.5 and 5% with respect to the total weight of the composition.

Among the preferred antibiotic substances one can cite erythromycin and its salts, clindamycin and its salts, and lincomycin and its salts.

In the treatment of acne, the compositions such as those defined hereinabove are applied at least once a day on the lesions at a rate of 0.5 to 10 mg/cm$^2$, the duration of treatment being on the order of 2 to 4 weeks, depending on the extent and degree of severity of the skin problem.

By way of illustration and without any limiting character, several examples of antiacne compositions according to the invention are now given.

EXAMPLE 1

An antiacne gel is prepared according to the invention by mixing the following ingredients:

| | |
|---|---|
| benzoyl peroxide | 10 g |
| 2-hydroxy-4-methoxybenzophenone-5-sulfonic acid | .1 g |
| 2-phenylbenzimidazole-5-sulfonic acid | 1 g |
| sodium q.s., pH 6 | |
| hydroxyethyl cellulose | 3 g |
| methyl para-hydroxybenzoate | 0.15 g |
| propylene glycol | 10 g |
| water, q.s.p. | 100 g |

This gel is obtained by first dissolving the two sun filters in water, then the methyl para-hydroxybenzoate. To the resulting mixture, one then adds the hydroxyethyl cellulose, then the propylene glycol. In the gel thus obtained, one then disperses the benzoyl peroxide after pulverizing.

EXAMPLE 2

An antiacne gel is prepared according to the invention by mixing the following ingredients:

| | |
|---|---|
| benzoyl peroxide | 5 g |
| 2-hydroxy-4-methoxybenzophenone-5-sulfonic acid | 1 g |
| 2-phenylbenzimidazole-5-sulfonic acid | 1 g |
| Carbopol 940 | 0.9 g |
| triethanolamine, q.s., pH 6 | |
| glycerol | 12 g |
| methyl para-hydroxybenzoate | 0.15 g |
| water + ethanol (80/20), q.s.p. | 100 g |

In this example, one can replace the 2-phenylbenzimidazole-5-sulfonic acid by benzylidenecamphor at a concentration of 1.5%. One can also replace the two sun filters by a single filter, i.e.:

1,4-bis-phenylene(3-methylene-10-camphosulfonic)acid or 3-[4-(2-oxo-3-bornylidene-methyl)benzylidene]-10-camphosulfonic acid, used either in acid form or in the form of its salt with a mineral or organic base (salt of Na, of K, of triethanolamine), said filter being used at a concentration of 1.5%.

EXAMPLE 3

An antiacne cream is prepared according to the invention in the form of an oil-in-water emulsion by mixing the following ingredients:

| | |
|---|---|
| benzoyl peroxide | 10 g |
| titanium dioxide | 2 g |

-continued

| | |
|---|---|
| Timica Silkwhite | 3 g |
| polyethylene glycol stearate | 4 g |
| benzylidenecamphor | 1 g |
| glycerol monostearate | 1 g |
| cetyl alcohol | 2 g |
| sweet almond oil | 5 g |
| Sinnowax SX (a mixture of 90% stearyl alcohol and 10% Na lauryl sulfate) | 4 g |
| methyl para-hydroxybenzoate | 0.2 g |
| perhydrosqualene | 5 g |
| water, q.s.p. | 100 g |

EXAMPLE 4

Anantiacne cream is prepared according to the invention in the form of a water-in-oil emulsion by mixing the following ingredients:

| | |
|---|---|
| benzoyl peroxide | 10 g |
| 2-hydroxy-4-methoxybenzophenone | 1.5 g |
| 2-ethylhexyl p-dimethylaminobenzoate | 1.5 g |
| "Protegin X"[1] sold by the GOLDSCHMIDT Company | 20 g |
| vaseline oil | 10 g |
| methyl para-hydroxybenzoate | 0.2 g |
| propyl para-hydroxybenzoate | 0.2 g |
| glycerol | 5 g |
| magnesium sulfate | 0.5 g |
| water, q.s.p. | 100 g |

[1]"Protegin X" - mixture of mineral oil, vaseline, ozokerite, glyceryl oleate, and lanolin alcohols.

EXAMPLE 5

An antiacne gel is prepared according to the invention by mixing the following ingredients:

| | |
|---|---|
| Carbopol 940 | 1 g |
| triethanolamine | 1 g |
| propylene glycol | 5 g |
| methyl p-hydroxybenzoate | 0.15 g |
| benzoyl peroxide | 10 g |
| titanium dioxide | 2 g |
| Timica silkwhite | 3 g |
| 2-phenylbenzimidazole-5-sulfonic acid | 1.5 g |
| water, q.s.p. | 100 g |

EXAMPLE 6

An antiacne composition is prepared according to the invention by mixing the following ingredients:

| | |
|---|---|
| Carbopol 940 | 0.8 g |
| Aerosil 200 | 0.021 g |
| propylene glycol | 4.0 g |
| Triton GR 5M (sodium salt of the diester of 2-ethylhexyl alcohol and sulfosuccinic acid) | 0.08 g |
| Pluronic L 62 (polycondensate of ethylene oxide and polypropylene glycol) | 0.2 g |
| EDTA, disodium | 0.1 g |
| 10% soda, q.s.p. pH = 5.3 | |
| benzoyl peroxide | 10 g |
| 2-phenylbenzimidazole-5-sulfonic acid | 1 g |
| water, q.s.p. | 100 g |

EXAMPLE 7

An antiacne composition is prepared according to the invention by mixing the following ingredients:

| | |
|---|---|
| Carbopol 940 | 1 g |
| triethanolamine | 1 g |
| propylene glycol | 3 g |
| methyl para-hydroxybenzoate | 0.1 g |
| sodium dioctyl sulfosuccinate | 0.05 g |
| Aerosil 200 | 1 g |
| benzoyl peroxide | 10 g |
| 2-hydroxy-4-methoxybenzophenone-5-sulfonic acid | 1 g |
| 2-phenylbenzimidazole-5-sulfonic acid | 1 g |
| EDTA, disodium | 0.05 g |
| water, q.s.p. | 100 g |

EXAMPLE 8

An antiacne composition containing an antibiotic in association is prepared according to the invention by mixing the following ingredients:

| | |
|---|---|
| Carbopol 940 | 1 g |
| sodium hydroxide, q.s.p.   pH = 5.4 | |
| propylene glycol | 5 g |
| EDTA, disodium | 0.01 g |
| polyoxyethylenated lauryl alcohol | 3 g |
| methyl para-hydroxybenzoate | 0.15 g |
| benzoyl peroxide | 10 g |
| clindamycin phosphate | 2 g |
| diethanolamine p-methoxycinnamate | 1 g |
| water, q.s.p. | 100 g |

What is claimed is:

1. A composition for the local treatment of acne comprising 0.5 to 20% by weight of benzoyl peroxide and 0.1 to 10% by weight of a sun filter selected from the group consisting of:

(i) a benzylidene camphor derivative of the formula:

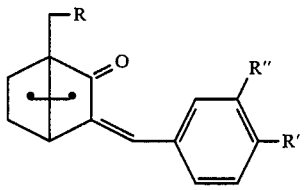

wherein R is selected from the group consisting of a hydrogen atom, —SO₃H, and pharmaceutically acceptable salts thereof, and SO₂NH—R₁, where R₁ is a linear or branched alkyl radical having 1 to 12 carbon atoms, R' is selected from the group consisting of: hydrogen atom; alkyl radical having 1 to 4 carbon atoms; alkoxy having 1 to 18 carbon atoms; —N(CH₃)₃; —SO₃H and pharmaceutically acceptable salts thereof; —SO₂NH—R₂, wherein R₂ is 2-ethylhexyl; —CH=C(CO₂R₃)₂, wherein R₃ is an alkyl radical having 1 to 12 carbon atoms; a radical of the formula:

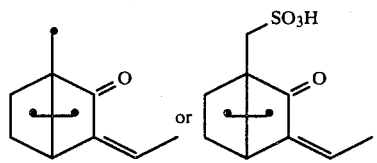

and R" is selected from the group consisting of hydrogen atom, alkoxy having 1 to 4 carbon atoms, —SO₃H and pharmaceutically acceptable salts thereof when R' is alkyl or alkoxy, (ii) 2-phenylbenzimidazole-5 sulfonic acid and pharmaceutically acceptable salts thereof, (iii) 2-hydroxybenzophenone derivatives selected from the group consisting of 2-hydroxy-4-methoxybenzophenone, 2-hydroxy-4-methoxybenzophenone-5-sulfonic acid and pharmaceutically acceptable salts thereof, and (iv) cinnamic acid derivatives selected from the group consisting of diethanolamine p-methoxycinnamate and 2-ethylhexyl p-methoxycinnamate.

2. The composition of claim 1 wherein said benzoyl peroxide is present in an amount of 2.5 to 10% by weight with respect to the total weight of the composition.

3. The composition of claim 1 wherein said benzylidene camphor derivative is selected from the group consisting of p-tolylidenecamphor, trimethylammoniobenzylidenecamphor methyl sulfate, 4-isopropylbenzylidenecamphor, 4-[2-oxo-3-bornylidenemethyl]benzenesulfonic acid, 2-methyl-5-(2-oxo-3-bornylidenemethyl benzenesulfonic acid, N-(2-ethylhexyl)-3-benzylidene-10-camphosulfonamide, 3-[4-(2-oxo-3-bornylidenemethyl)benzylidene]-10-camphosulfonic acid, 1,4-bis-phenylene(3-methylene-10-camphosulfonic)acid, ethyl p-(2-oxo-3-bornylidenemethyl)benzylidenemalonate, p-methoxy-3-benzylidene-10-camphosulfonic acid, 3-benzylidene-2-oxo-10-boranesulfonic acid, N-(2-ethylhexyl)-p-methoxy-3-benzylidene-10-camphosulfonamide, 4'-butoxy-3'-methoxy-3-benzylidene-2-oxobornane and the pharmaceutically acceptable salts of said acids.

4. The composition of claim 1 further comprising a metallic oxide selected from the group consisting of zinc oxide and titanium oxide.

5. The composition of claim 1 further comprising an anti-acne substance selected from the group consisting of erythromycin, clindamycin, lincomycin, and the pharmaceutically acceptable salts thereof.

* * * * *